United States Patent [19]

Uesugi

[11] Patent Number: 5,178,828
[45] Date of Patent: Jan. 12, 1993

[54] APPARATUS FOR TREATMENT OF MEDICAL WASTE MATERIALS

[75] Inventor: Jun Uesugi, Ichigawa, Japan

[73] Assignee: Shin-ichi Koyama, Kanagawa, Japan

[21] Appl. No.: 618,256

[22] Filed: Nov. 21, 1990

[51] Int. Cl.$^5$ .................... A61L 2/06; B65B 55/00
[52] U.S. Cl. ........................ 422/22; 422/288; 110/238
[58] Field of Search ............... 422/22, 288; 110/238

[56] References Cited

U.S. PATENT DOCUMENTS

| | | | |
|---|---|---|---|
| 4,050,900 | 9/1977 | Hobbs et al. | 110/190 |
| 4,960,380 | 10/1990 | Cheetham | 110/255 |
| 5,019,344 | 5/1991 | Kutner et al. | 422/21 |
| 5,035,858 | 7/1991 | Held et al. | 422/21 |

Primary Examiner—James C. Housel
Assistant Examiner—Lyle A. Alexander
Attorney, Agent, or Firm—Staas & Halsey

[57] ABSTRACT

Medical waste material is sealed in a nonflammable and long infrared radiation pervious film bag. The bag is subjected to long infrared radiation by an apparatus for a sufficient period of time at sterilizing temperature levels. Any smoke and odor generated during sterilization is treated.

9 Claims, 7 Drawing Sheets

APPARATUS FOR TREATMENT OF MEDICAL WASTE MATERIALS

BACKGROUND OF THE INVENTION

This invention relates to an apparatus for treatment of medical waste materials, and more particularly to the treatment and disposal of medical waste using plastic film bags.

There are significant known difficulties and limitations associated with off-site disposal of medical waste including high cost. As a result, there are incentives for many health care and other institutions to consider or select on-site incineration as the preferred medical waste treatment. For many institutions, particularly hospitals or practitioners, incineration is the only viable technology available for treating the increased volume of waste. Unfortunately, on-site treatment is not usually a viable alternative due to, among other things, the smoke and odor produced.

SUMMARY OF THE INVENTION

Accordingly, it is a purpose of the present invention to provide a novel apparatus and method to resolve these serious circumstances.

It is another object to provide an apparatus to sterilize pathogenic waste, to detoxify chemical waste, and to convert noxious waste into innocuous material.

It is another object to provide an apparatus facilitating treatment and disposal of medical waste so that human involvement is minimized and humans are protected against exposure to infectious or horrible disease during handling and transportation.

Finally, the present invention has the object of providing an apparatus to effectively and promptly treat and dispose of medical waste materials without having to store the waste materials for a long period of time.

To achieve the foregoing and other purposes of the present invention there is provided an apparatus and method to treat and dispose of medical waste using a heat-resistent film bag into which medical waste is placed and the bag is sealed. The waste and bag are heated to a sterilization temperature of 180 degrees C. to 250 degrees C. using long infrared radiation produced by infrared panels in a sterilization chamber to sterilize the infectious medical waste. As used herein, the term "long infrared radiation" refers to infrared radiation having a wavelength in the range from about 14,000 Å to about 150,000 Å. After confirmation of sterilization, during which time smoke and odor are produced, the waste is disposed of safely. The odor and smoke problem is solved through the following means: air suction by a pneumatic blower, ozone injection for oxidation by an ozonizer, water washing, deodorizing and filtering. Thus smoke and odor are successfully removed and the atmosphere is kept clean without incurring any pollution at all.

The combination of long infrared radiation, the film bag, deodorant and filter results in odorless, clean treatment of medical waste.

This invention therefore provides an apparatus to dispose of the medical waste using a safe on-site method, wherein human intervention is minimized. The apparatus is also designed to reduce the weight and volume of most institutional solid waste, to sterilize pathogenic waste, to detoxify chemical waste, and to convert noxious waste into innocuous material.

At most institutions, these factors provide a substantial reduction in off-site disposal costs such that on-site incineration is highly cost-effective. In addition, on-site incineration reduces dependence upon off-site disposal contracts which, in turn, minimizes potential exposure and liabilities associated with illegal or improper waste disposal activities.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENT

Figure 1:
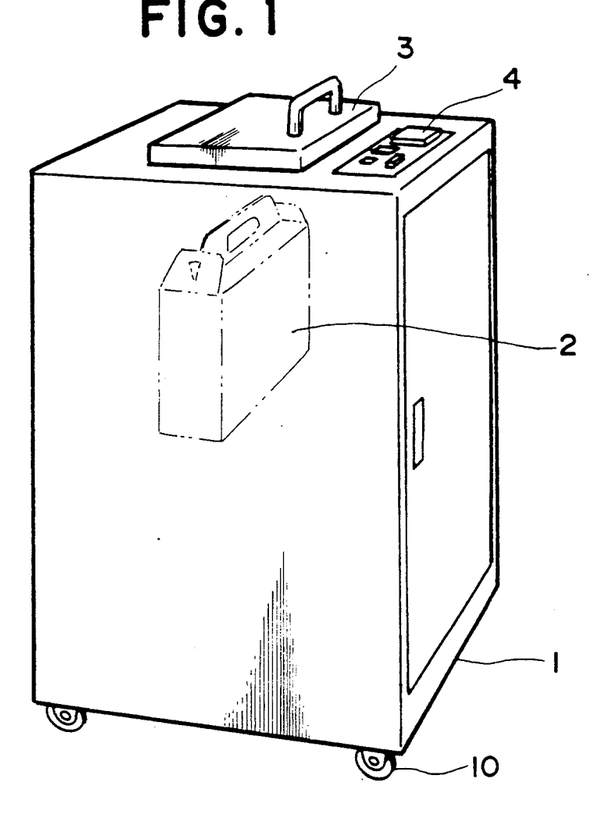
FIG. 1 is a perspective view of the apparatus according to the present invention.
Figure 3:
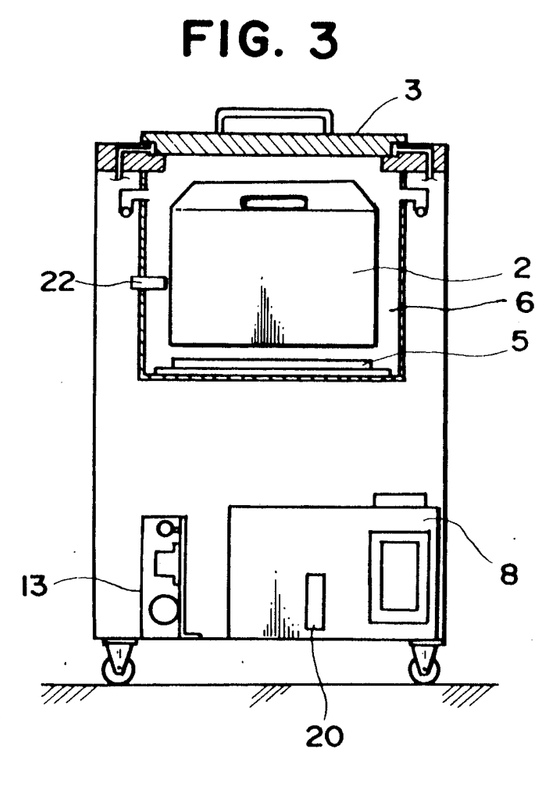
FIG. 3 is a sectional side elevation of the apparatus.
Figure 4:
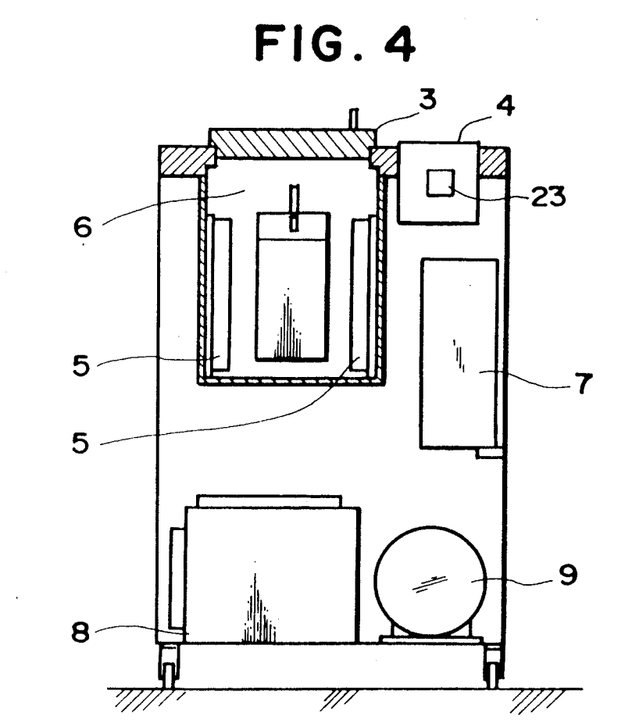
FIG. 4 is another sectional side elevation of the apparatus.

With reference to FIGS. 1, 3 and 4 numeral 1 shows the body of an apparatus of this invention, which contains a film bag 2 inside. The apparatus has an upper lid 3, an operation panel 4, a control panel 7, and a set of casters 10 on the bottom for easy movement.

Figure 2:
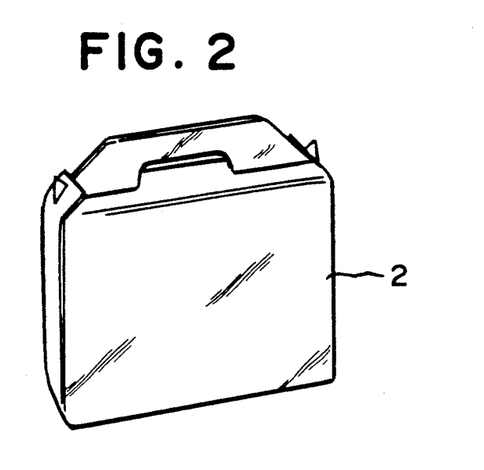
FIG. 2 is a total perspective view of a film bag according to the present invention.

The preferred dimensions of this apparatus are 660 mm×650 mm×1,000 mm for compactness. The preferred dimensions of the film bag 2 are 130 mm×300 mm×250 mm with approximately 10 liters capacity. According to actual use requirements, the size of the apparatus and film bag 2 can be changed without parting from the scope of this invention.

FIG. 2 shows an outer appearance of the film bag 2 which is a nonflammable bag constructed from plastic film. This film bag 2 is preferably a laminate having an inner layer made of about 50 micron thickness of polyethylene and an outer layer made of about 50 micron thickness polyester for added strength. The two materials are laminated by ultrasonic waves. The bag is rigid, leak resistant, impervious to moisture and has enough strength to prevent tearing or bursting under normal conditions of use and handling of sharp objects and residual fluids. The sharp objects which can be accommodated by the bag 2 include objects that have been used in human patient care or treatment or in medical research or industrial laboratories, including injection needles and broken or unbroken glassware that have been in contact with infectious agents.

In accordance with the present invention, the film bag 2 must be pervious to long wavelength infrared radiation. In other words, it must allow long infrared radiation to pass through. Moreover, the bag must be nonflammable in the sense that its physical appearance and condition are preserved after it is subjected to the heating and sterilizing operations.

With reference to FIG. 3 and FIG. 4, medical wastes are put into the film bag 2 and the bag is sealed by, e.g. two sided adhesive tape. Sealing prevents particles from leaving the bag during sterilization. Then, the upper lid 3 is opened, the bag 2 is placed in a heat sterilizing chamber 6, and the lid 3 is closed. The main power switch is then turned "ON". The desired sterilizing temperature and time duration is set on the operation panel 4 and is displayed digitally on the panel 4. Then a start button is pressed. Operation thereafter is fully automatic.

The setting of sterilizing temperature and time is according to the guidelines below:

| STANDARD TEMPERATURES AND TIME | | |
| --- | --- | --- |
| Kind of Medical Waste | Sterilizing Temp. | Sterilizing Time |
| Syringes, Needles | 180 degrees C. | 30 minutes |
| Bandages, Sanitary Cotton, Operating Stitches | 180 degrees C. | 30 minutes |
| Blood Transfusions | 180 degrees C. | 40 minutes |
| Blood vials, Blood Dialyzer | 180 degrees C. | 30 minutes |
| All Kinds of Tubes, Caps | 180 degrees C. | 30 minutes |
| All Kinds of Culture Dishes | 180 degrees C. | 30 minutes |
| Blood, Blood Clots | 180 degrees C. | 40 minutes |
| Test Tubes, Used Slides | 180 degrees C. | 40 minutes |
| Scalpel Blades Stitching Needles | 180 degrees C. | 30 minutes |

The proposed sterilization temperatures above, are based on academic research and theories. In this regard, horrible diseases such as AIDS or HEPATITIS-B have been reported and shown to be communicable to humans through treatment and handling such waste materials. For instance, HEPATITIS-B virus is said to become inert after being subjected to 60 degrees C. for 30 minutes. However, the World Health Organization requires that this virus be heated at 120 degrees C. for 30 minutes followed by treatment with ethylene oxide. With reference to the AIDS virus, the present academic research reports that it dies in the air. However, it is, of course, advisable and recommended that such virus also should be subjected to heating to make sure that the virus is killed in due course.

A high temperature atmosphere in a long infrared radiation panel housed chamber can kill infectious bacteria and virus in every area of the film bag, and it also can assure exact sterilization.

Progress of the operation can be confirmed on the display panel of the operation panel 4 in the following order: temperature increase, sterilization, temperature decrease (cooling) and completion.

On the inner wall of the heat sterilizing chamber 6, plural long infrared heater panels 5 are positioned, and desired temperature increase and temperature maintenance are automatically controlled by a sensor 22 in the range of 180 degrees C. to 250 degrees C. The sterilizing time is also controlled by a timer 23 in the range of up to 99 minutes. The timer 23 is built into the control panel and is run by sequential control electronically.

Figure 5:
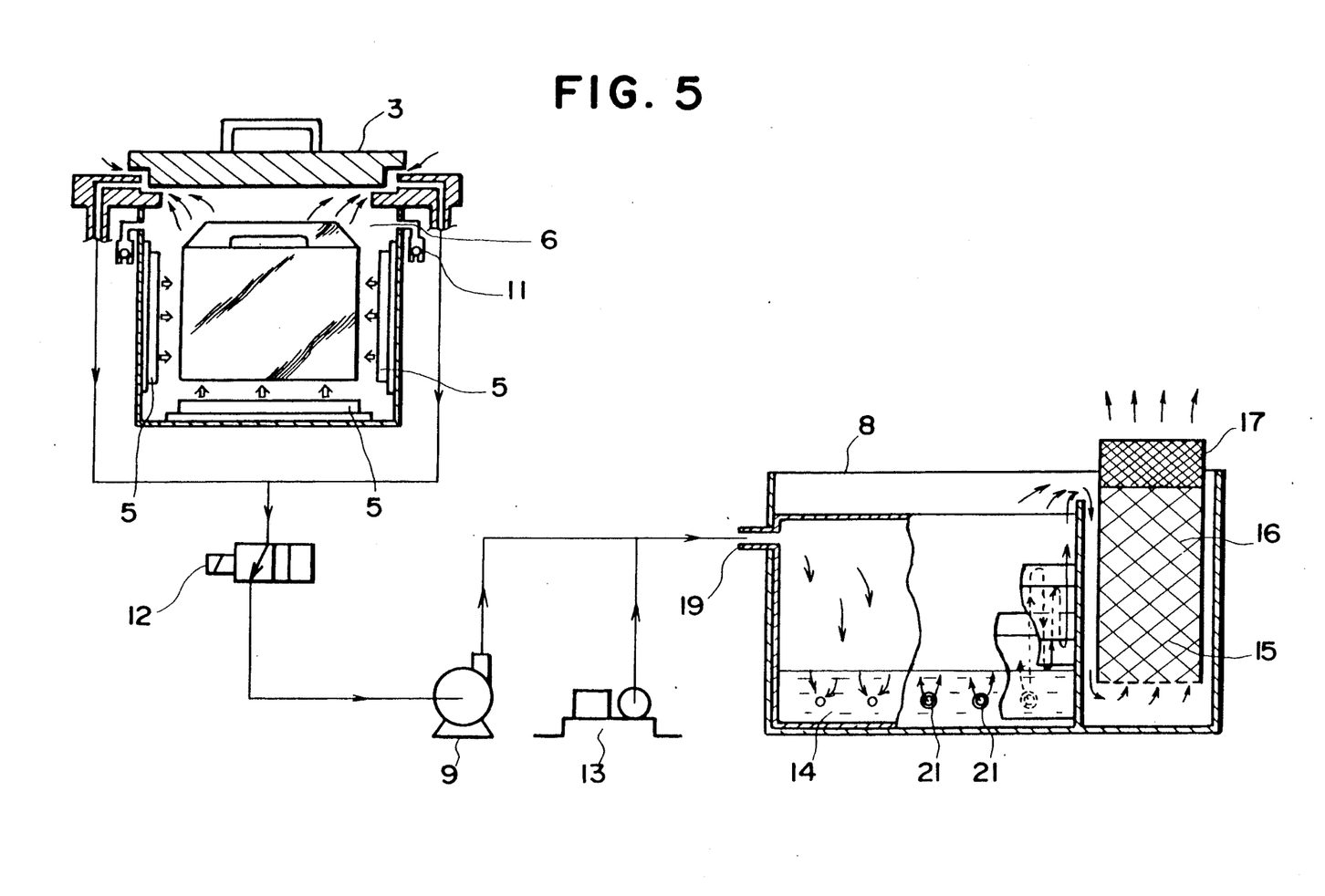
FIG. 5 and FIG. 6 are partial sectional views showing the deodorizing procedure.

Removing foul odor and smoke is done by the following steps. With reference to FIG. 5, odor and smoke in the heat sterilizing chamber 6 are air-suctioned by a pneumatic blower 9 by opening an electromagnetic valve 12. In order to oxidize the atmospheric air, ozone is injected from an ozonizer 13 during the movement of the smoke and odor from the heat sterilizing chamber 6 to a deodorizing means 8. In order to avoid a back current of the odor and smoke into the heat sterilizing chamber 6, a back current prevention valve 11 is located on the outside of the chamber 6.

The odor and smoke coming through an entrance 19 of the deodorizing means 8 are mixed and washed in a gas-liquid mixing tub 14, where they are converted into alkaline by water, and then pass through a deodorizing agent layer 15 and an ozanant catalyst layer 16. Finally, before air is exhausted to atmosphere, micro particles are removed by a mini-HEPA filter 17. Through this process, smoke and odor are successfully removed and thus the atmospheric air is kept clean when the gas running through the above apparatus is released.

With reference to FIGS. 6-9, the deodorizing means is explained in greater detail.

Figure 6:
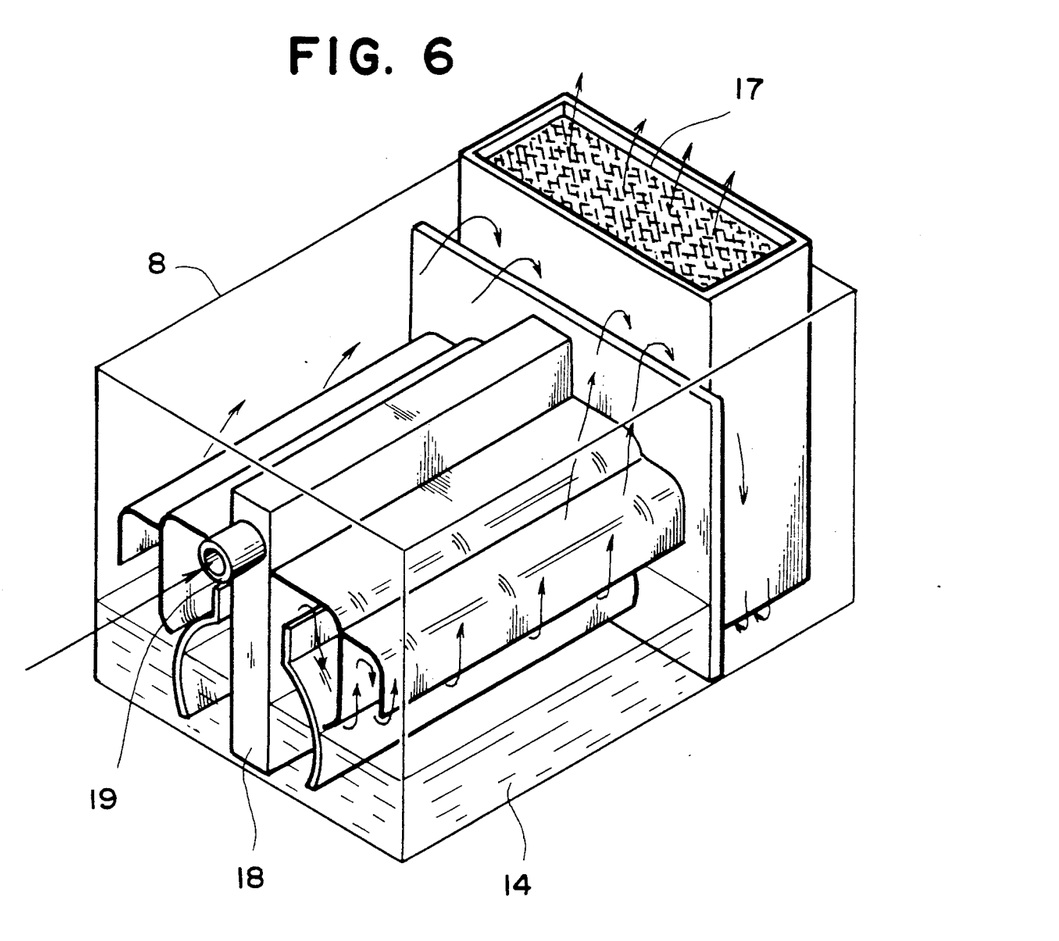

Referring to FIG. 6, foul odor and smoke are forcibly transferred via the entrance 19 into the gas-liquid mixing tub 14 by the operation of a vaporizer 18, whereon they are subject to water washing. Any odor and smoke remaining after the mixing and washing steps described above passes through the deodorizing agent layer 15, the ozonant catalyst layer 16 and finally the filter 17. As a result, odor and smoke are removed and the treated gas is released in a clean condition.

Figure 7:
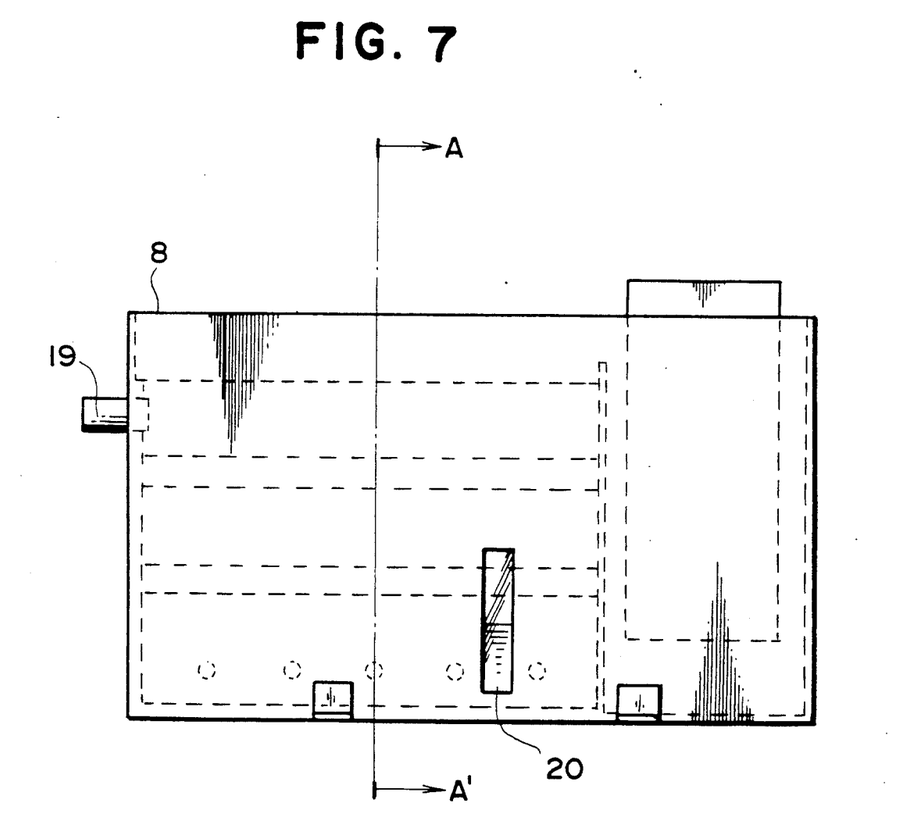
FIG. 7 is a side view of washing means used in the process of deodorization.

FIG. 7 shows a sectional view of the deodorizing means 8, with a window 20 formed thereon, from which the water level is confirmed before starting the operation.

Figure 8:
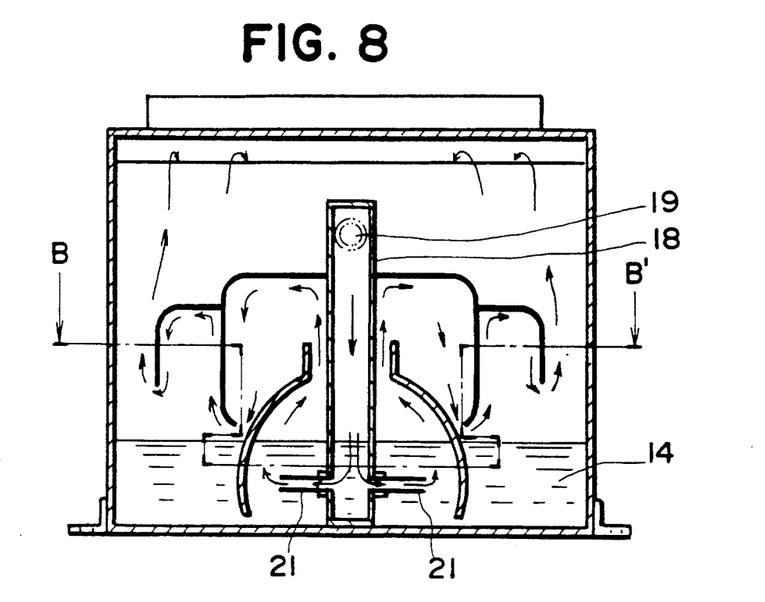
FIG. 8 is a sectional view taken along line A—A' of FIG. 7.

FIG. 8 shows the operation of the vaporizer 18 which drives foul odor and smoke into the gas-liquid mixing tub 14 for washing, and then to the deodorizing agent layer 15.

Figure 9:
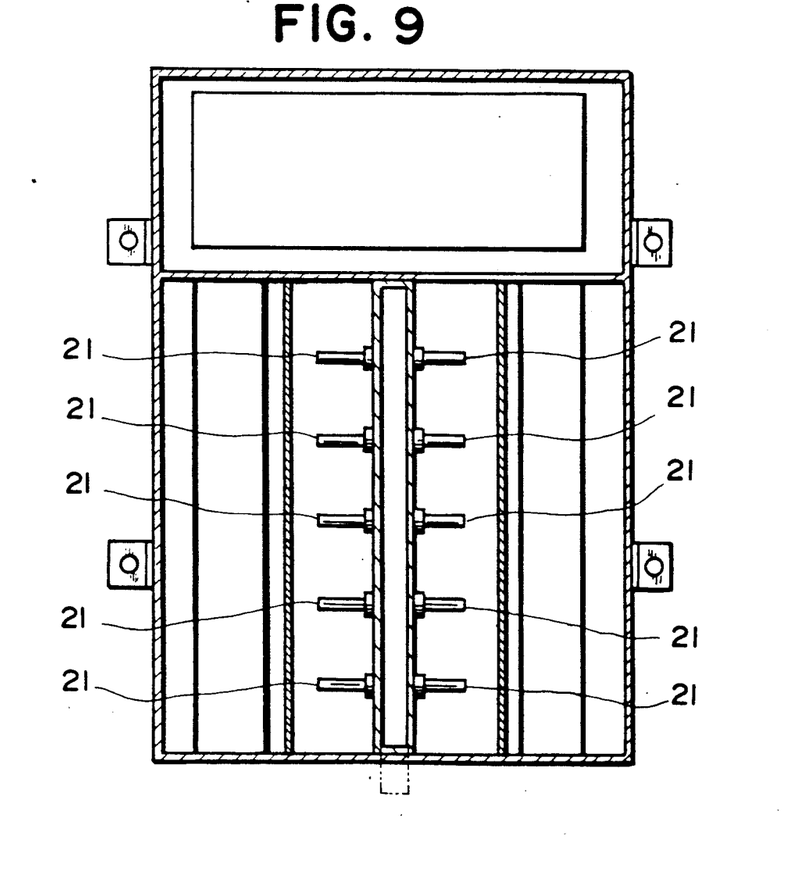
FIG. 9 is a sectional view taken along line B-B' of FIG. 8.

FIGS. 5 and 9 show the vaporizer 18 working with plural nozzles 21.

Simultaneous to the above odor and smoke removal procedure, a cooling procedure occurs for the heat sterilizing chamber 6 under the operation of the blower 9 and the electromagnetic valve 12. When cooling is completed, as confirmed on the panel 4, the film bag 2 is taken out and disposed.

Figure 10:
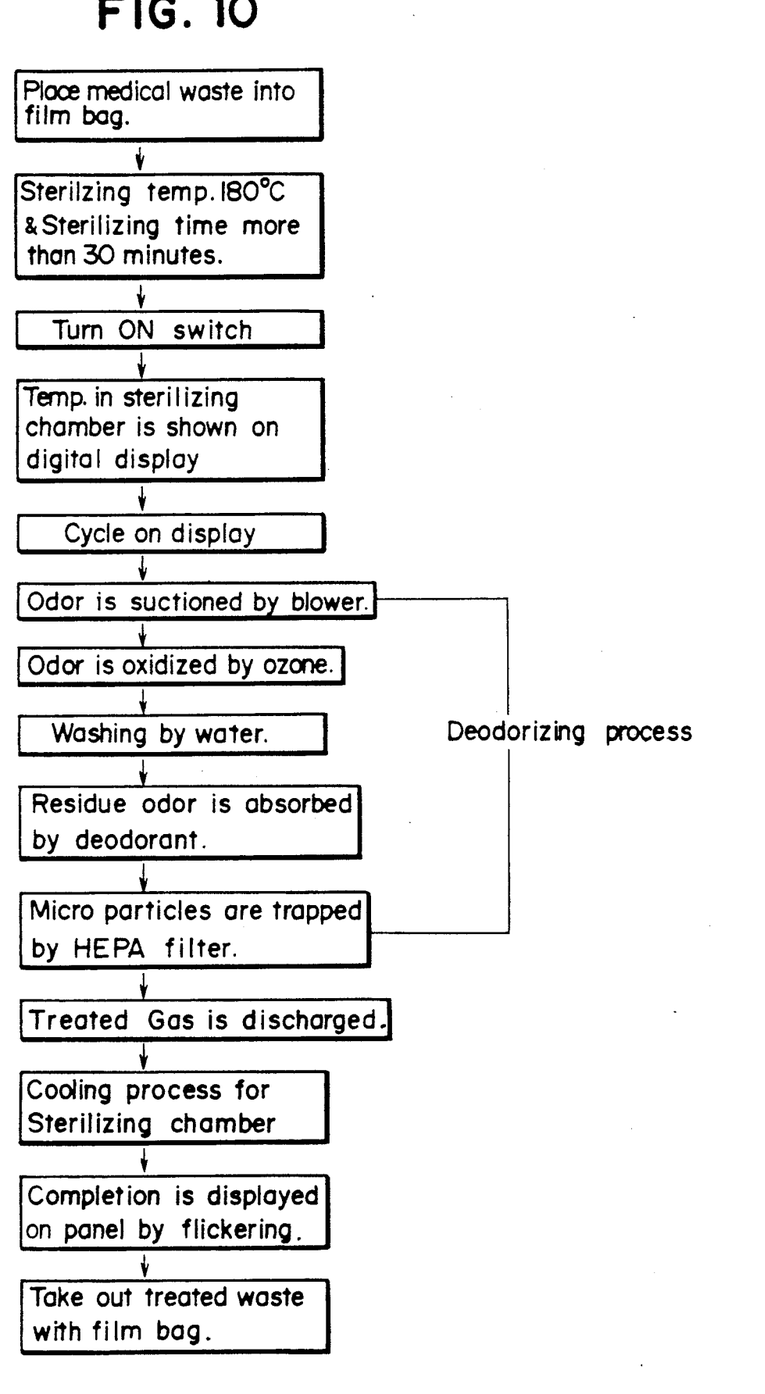
FIG. 10 is a flowchart showing the method according to the present invention.

FIG. 10 illustrates the method according to the present invention. In step 1, medical waste is placed into the film bag. In step 2, the sterilizing temperature is set at about 180° C. and the sterilizing time is set to at least 30 minutes. In step 3, the switch is turned to ON. In step 4, the temperature in the sterilizing chamber is displayed. In step 5, the cycle, i.e., temperature increase, sterilization, cooling and completion is shown on the display. In step 6, the odor and smoke are suctioned by the blower. Then in step 7, the odor and smoke are oxidized by ozone. In step 8, the odor and smoke are washed by water. In step 9, any residual odor and smoke are absorbed by deodorant and in step 10, any micro particles, for example, particles of smoke, are trapped by the Hepa filter In step 11, the treated gas is discharged from the apparatus. In step 12, the sterilizing chamber is cooled. In step 13, the display panel indicates completion of the sterilization process Finally, in step 14, the film bag including the treated waste is removed from the apparatus. During the sterilization, the smoke and odor are removed as by products as the temperature increases. This apparatus makes possible sterilization, while efficiently removing smoke and odor.

The foregoing is considered illustrative only of the principles of the invention. For example, with regard to the film bag, the invention is not limited only to the use of the bag described. The important features are that it be a receptacle pervious to long infrared radiation and the heating procedures should not cause any damage or disrupt the original form of the receptacle to any substantial extent. The receptacle should also be sturdy enough to keep needles, metal pieces, broken glass, and the like, from passing through the wall of the receptacle during processing. Accordingly, the receptacle can be constructed of other materials such as cardboard, ceramics, etc. Further, since numerous modifications and changes will readily occur to those skilled in the art, it is not desired to limit the invention to the exact construction and operation shown and described. Accordingly, all suitable modifications and equivalents may be resorted to that fall within the scope of the invention and the appended claims.

What is claimed is:

1. Combination of a receptacle for medical waste material and an apparatus for treatment of the medical waste material, comprising:
    a sealed, nonflammable, long infrared radiation and smoke and odor pervious film bag receptacle for receiving only the medical waste material;
    a sterilization chamber including means for subjecting the film bag and the waste material to long infrared radiation at a temperature of up to about 220° for up to about 30 minutes to sterilize the medical waste material; and
    means for removing smoke and odor generated in the chamber during the sterilization of the medical waste material.

2. Combination according to claim 1, wherein said sterilization chamber has interior wall surfaces and said means for subjecting the film bag receptacle and the medical waste material in the receptacle to long infrared radiation includes a plurality of long infrared radiation heater elements mounted on said interior surfaces.

3. Combination according to claim 1, further comprising:
    means in the chamber for sensing the temperature therein to insure the maintenance of a preset sterilization temperature for a predetermined period of time.

4. Combination according to claim 1, wherein said means for removing smoke and odor comprises:
    a vaporizer in air communication with the chamber and equipped with a plurality of vaporizing nozzles;
    a gas-liquid mixing tub including liquid at a lower portion thereof for receiving a portion of the vaporizer equipped with the nozzles, wherein gases from the chamber are emitted into the liquid in the tub via the nozzles; and
    a filter device in air communication with the upper portion of the tub, including
        a deodorizing agent layer;
        a lower ozonant catalyst layer; and
        an intermediate filter layer.

5. Combination according to claim 4, wherein smoke and odor generated in said sterilizing chamber are washed in said gas-liquid mixing tub by operation of said vaporizer and the treated gas is released outside the apparatus after passing through said deodorizing agent layer, ozonant catalyst layer and filter layer.

6. Combination according to claim 4, wherein water is used in said gas-liquid mixing tub.

7. Combination of a receptacle for medical waste material and an apparatus for treatment of the medical waste material, comprising:
    a sealed, nonflammable, long infrared radiation and smoke and odor pervious film bag receptacle for receiving only the medical waste material;
    a sterilization chamber including means for subjecting the film bag and the medical waste material to long infrared radiation causing a temperature of 180° to 250° C. for up to about 30 minutes to sterilize the medical waste material,
    deodorizing means operated by a blower via an ozonizer to remove smoke and odor generated during the sterilization of the medical waste material; and
    means to dissipate treated gas after cleaning via said deodorizing means.

8. Method for treating medical waste material, comprising the steps of:
    placing a sealed, nonflammable, long infrared radiation and smoke and odor pervious film bag with only medical waste material therein in a sterilization chamber;
    subjecting the container and the medical waste material to long infrared radiation causing a temperature of up to about 220° C. for up to about 30 minutes to sterilize the medical waste material; and
    removing smoke and odor generated in the chamber during the sterilization of the medical waste material.

9. Method according to claim 8, further comprising the step of:
    sensing the temperature in the chamber to insure the maintenance of a preset sterilization temperature for a predetermined period of time.

* * * * *